United States Patent [19]

Krause et al.

[11] Patent Number: 4,493,697

[45] Date of Patent: * Jan. 15, 1985

[54] METHOD AND APPARATUS FOR PUMPING BLOOD WITHIN A VESSEL

[76] Inventors: Horst E. Krause, P.O. Box 617, Freeport, Tex. 77541; Edwin L. Stanley, 2566 S. Patterson Blvd., Dayton, Ohio 45409

[*] Notice: The portion of the term of this patent subsequent to May 15, 1996 has been disclaimed.

[21] Appl. No.: 292,991

[22] Filed: Aug. 14, 1981

Related U.S. Application Data

[63] Continuation-in-part of Ser. No. 037,766, May 10, 1979, Pat. No. 4,284,073, which is a continuation of Ser. No. 841,017, Oct. 11, 1977, Pat. No. 4,154,227.

[51] Int. Cl.³ .............................................. A61M 1/03
[52] U.S. Cl. .................................. 604/50; 128/1 D; 128/66; 604/53; 604/67; 604/151
[58] Field of Search ............... 128/1 D, 214 R, 214 F, 128/348, DIG. 3, 66; 604/28, 49, 50, 53, 67, 151

[56] References Cited

U.S. PATENT DOCUMENTS

| | | | |
|---|---|---|---|
| 1,846,596 | 2/1932 | Hertzberg | 128/227 |
| 2,925,814 | 2/1960 | Vibber et al. | 128/214 F |
| 3,021,793 | 2/1962 | Bolstad | 128/1 D X |
| 3,099,260 | 7/1963 | Birtwell | 128/1 D |
| 3,266,487 | 8/1966 | Watkins et al. | 128/1 D |
| 3,421,497 | 1/1969 | Chesnut et al. | 128/1 D |
| 3,505,987 | 4/1970 | Heilman | 128/1 D |
| 3,877,843 | 4/1975 | Fischel | 128/1 D |
| 3,993,054 | 11/1976 | Newman | 128/66 |
| 3,995,617 | 12/1976 | Watkins et al. | 128/1 D |
| 4,080,958 | 3/1978 | Bregman et al. | 128/1 D |

Primary Examiner—Dalton L. Truluck
Attorney, Agent, or Firm—Jacox & Meckstroth

[57] ABSTRACT

A dynamically augmenting pump system incorporates a sealed liquid-filled catheter which is inserted into a vessel such as an artery, and the pump system is operated in timed relation with the heart to aid the heart during episodes of impairment or failure of cardiac function by producing higher frequency pulsation or pressure waves within the blood during diastole and during the isometric contraction period of the heart. This frequency of pulsation is adjusted to the dynamic transmission characteristics of a selected circulatory subsystem, such as the coronary vascular system, to assure the transmission of a maximum of pulsatile energy into the subsystem. The catheter provides energy to maintain adequate blood flow through the healthy part of the myocardium and has a passage for injecting successive quantities of medication into the coronary arteries. The pump system also functions to penetrate the ischemic myocardial tissue with arterial blood and medication. The pump system may also be used to provide a flow of blood or substitute perfusates through selected tissues or body organs or to enhanced perfusion for other parts of the systemic circulatory system, for example, to prevent such detrimental effects as renal failure. Any one or combination of the functions may be used depending on the special medical conditions of the patient.

15 Claims, 8 Drawing Figures

METHOD AND APPARATUS FOR PUMPING BLOOD WITHIN A VESSEL

RELATED APPLICATION

This application is a continuation-in-part of U.S. application Ser. No. 037,766, filed May 10, 1979, now U.S. Pat. No. 4,284,073, which is a continuation of U.S. Ser. No. 841,017, filed Oct. 11, 1977, now U.S. Pat. No. 4,154,227.

SUMMARY OF THE INVENTION

The present invention is directed to a method and apparatus for pumping blood or substitute perfusates through selected tissues or organs of the human body. The flow of body or substitute perfusates in an isolated or in a vitro biological specimen is dynamically augmented by producing pressure and flow waves in the perfusing liquid of a frequency, amplitude, and pulse shape which are optimally adjusted to the dynamic properties of the specific vascular system under treatment. The transmission of a maximum of pulsatile energy into the peripheral vasculature results in a satisfactory perfusate (or medication) distribution in selected healthy or diseased tissue or organs. The optimum frequency of pulsation is greater than the normal heart beat frequency because the dimensions of a specific tissue area or an organ or organ systems are less than those of the entire body.

In one embodiment, a sealed liquid-filled catheter has a hydraulically inflatable bulbous tip and is inserted into a proper artery of a patient so that the tip is advanced close to the aortic valve. The catheter also has a small open-ended passage which facilitates the injection of medication or radiopaque solutions for angiographic purposes, and also transmits aortic pressure to an extracorporeal transducer for pressure recording. The primary liquid-filled catheter passage functions as a conduit to inject and withdraw the liquid from the inflatable tip so that the tip expands and collapses at a controlled higher frequency and in timed relation with the heart pulse.

The inflation of the catheter tip generates pressue waves in the aorta, and an oscilloscope displays the aortic pressure and a superimposed train of pressure waves. These waves travel in the proximal and distal directions thus transmitting energy in both directions. The energy transmitted towards the coronary arteries is greater than that transmitted distally. The resulting pressure amplitudes in the coronary arteries can be a multiple seven to ten times the natural pressure wave amplitude in the aorta if the frequency of tip inflation and deflation is properly adjusted to the transmission characteristics of the aorta and coronary arteries.

In another embodiment, one end of an open-ended catheter is inserted into an artery, a vein, or an artificial reservoir to draw blood or a substitute perfusate. The fluid passes through a pulsatile pumping device. The other open end of the catheter is inserted into any artery or vein of a specific section of tissue or an organ or a combination of organs. The catheter passage functions as a conduit to inject the blood or the substitute perfusate in a pulsatile manner of a controlled higher frequency, and if necessary, in timed relation with other events such as the heart pulse. The high frequency pulsatile delivery of perfusate results in pressure amplitudes in the small peripheral vessels of the perfused specimen. The pulsatile may be a multiple of the pressure wave amplitude at the exit of the catheter if the frequency of the pressure waves is properly adjusted to the transmission characteristics of the perfused vascular system. The system can be expanded by inserting a perfusate oxygenator, a heat exchanger, and a device for the controlled infusion of medication, and would normally be part of a closed loop or recirculating system.

Other features and advantages of the invention will be apparent from the following description, the accompanying drawings and the appended claims.

DESCRIPTION OF THE PREFERRED EMBODIMENT

Figure 1:
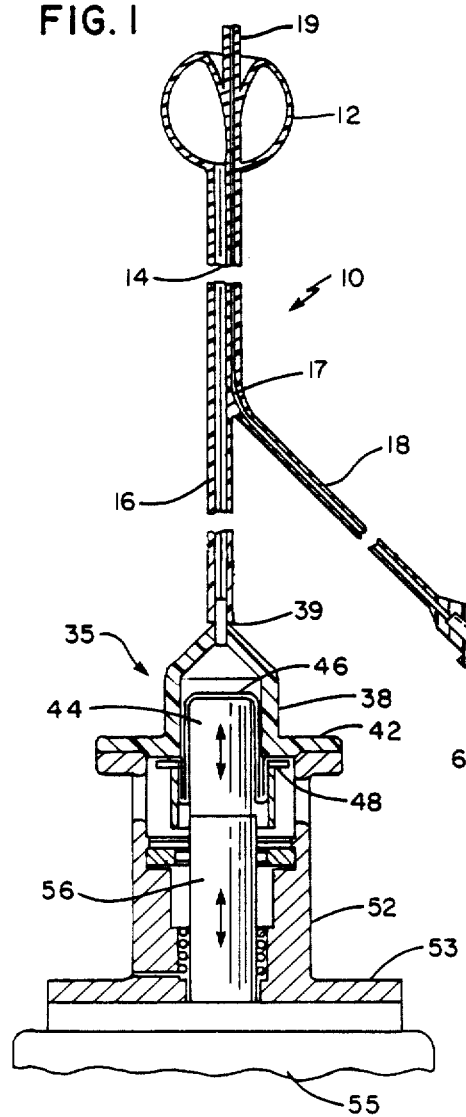
FIG. 1 illustrates an augmenting pump and medication pump system constructed in accordance with the invention and showing the sealed catheter in enlarged axial section with the tip portion inflated.
Figure 2:
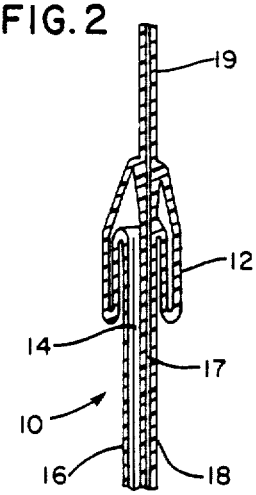
FIG. 2 is an enlarged axial section of the sealed catheter tip portion when deflated.
Figure 3:
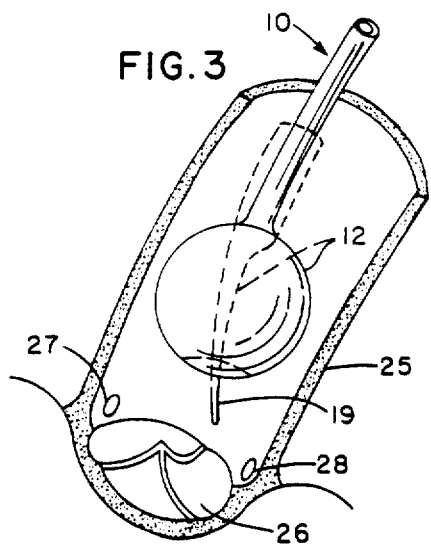
FIG. 3 illustrates the inflated and deflated sealed cather tip portion in the aorta adjacent the heart valves.

Referring to FIG. 1, a flexible catheter 10 is constructed of a non-resilient flexible material and includes a tip portion 12 which is inflatable between a collapsed condition (FIG. 2) and a generally spherical inflated condition with a center indentation (FIG. 1) when the tip portion has a volume of approximately three cubic centimeters. The tip portion 12 is inflated and deflated at a selected frequency by means of pumping and withdrawing a hydraulic fluid or liquid such as a saline solution through a primary passage 14 defined by a tubular portion 16. The catheter 10 also defines a smaller passage 17 which is defined by an integrally molded tubular portion 18 having a tip or end portion 19 which projects axially or forwardly from the inflatable tip portion 12 of the catheter. As illustrated in FIG. 3, the catheter 10 is inserted into a patient's artery so that the inflatable tip portion 12 is located within the aorta 25 close to the aortic valve 26. The pressure waves produced by inflating and deflating the tip portion 12 are effective to transmit the primary energy towards the coronary arteries 27 and 28.

The changes in position of the inflatable catheter tip portion 12 and/or the changes of the frequency of tip inflation and deflation provide control over the relative amounts of energy transmitted both forwardly and rearwardly. This permits vascular sections, either proximal or distal to the tip location, to be selected as the major recipients of pulsatile energy. The pulsatile energy substitutes for all or a part of the cardiac work reduction which occurs in cases of cardiac insufficiency. The beneficial effect of this energy in most cases of application is the intermittent elevation of blood pressure and flow momentum to normal levels in order to maintain some minimum penetration of high resistant vascular beds and tissue, thus minimizing the possibility of permanent organ or tissue damage.

The tissue of primary interest is the myocardium. Beneficial effects are provided for the intact part of the myocardium and the ischemic hypoxic part. The intact part of the myocardium will receive an adequate amount of blood through either alternating or stepwise increasing pressure and flow pulses during the diastolic period. The frequency of the pulses is adjusted according to the location of the tip portion 12 in relation to the coronary ostiae and the known transmission characteristics of the intermediate section of aorta and the coronary arteries in order to facilitate an optimum transmission of energy into the myocardium. A 10 Hz component is desirable, for example, if the tip portion 12 is placed close to the coronary ostiae.

Critical closing pressures at several levels are known in the myocardium. The highest levels of these critical closing pressures are exceeded by the pump system of the invention to produce a complete penetration of the healthy part of the myocardium. This is of particular importance for the subendocardial layers which offer the greatest resistance to flow and are most prone to damage in ischemia.

The subepicardial vasculature is completely closed during the systolic period through the squeezing effect of the contracted myocardial muscle. The epicardial vessels are patent because they are located in the epicardial surface rather than embedded in the myocardium. These vessels can receive blood during the systolic period but they cannot pass it on. Pressure and flow pulses inside the surface vessels are therefore reflected back and the superposition of incident and reflected waves produces high pressure values.

Collapsed collateral vessels exist normally between the major coronary arteries of the human heart, and are most numerous around the apex. The vessels are also known to be patent in some healthy humans, approximately 100 hours after an infarction, and occasionally after treatment with certain pharmaca prior to an infarct. The effect of generated elevated pressure pulses in accordance with the invention is the accelerated recruitment of collateral connections and the subsequent salvation of a greater mass of infarcted tissue than during the natural development of collateral connections.

The above treatment is aided by the injection of drugs through the medication catheter tube 18 and its projecting tip or end portion 19. The effects of these drugs are twofold. The amount of fluid passing through the initially opened collateral vessels is very small in comparison to the normal influx of blood into that area and may not be sufficient to avoid myocardial damage. The initially entering fluid, therefore, carries pharmaca which arrest the biochemical breakdown in the ischemic area before it becomes irreversible. Additional pharmacological agents may be applied to accelerate collateral development, in particular lumen increase, and assure an adequate supply of blood for the infarcted area at the earliest possible time.

The treatment of the ischemic myocardium requires the tip portion 12 to be inflated during the systolic period. However, the inflation must be limited to the isometric contraction period of the myocardium. The subepicardial vessels are already closed but the ventricle does not eject blood into the aorta 25. When this ejection occurs, the tip portion 12 is collapsed in order to decrease the ventricular afterload. This requirement and the necessary speed of operation due to the tip location and optimal tuning to cardiovascular dynamics requires a dynamically acting relatively small tip portion 12. The extracorporeal equipment for the control and timing of the tip portion performance is tuned to the dimensions and dynamics of the catheter 10 including the tip portion.

Figure 5:
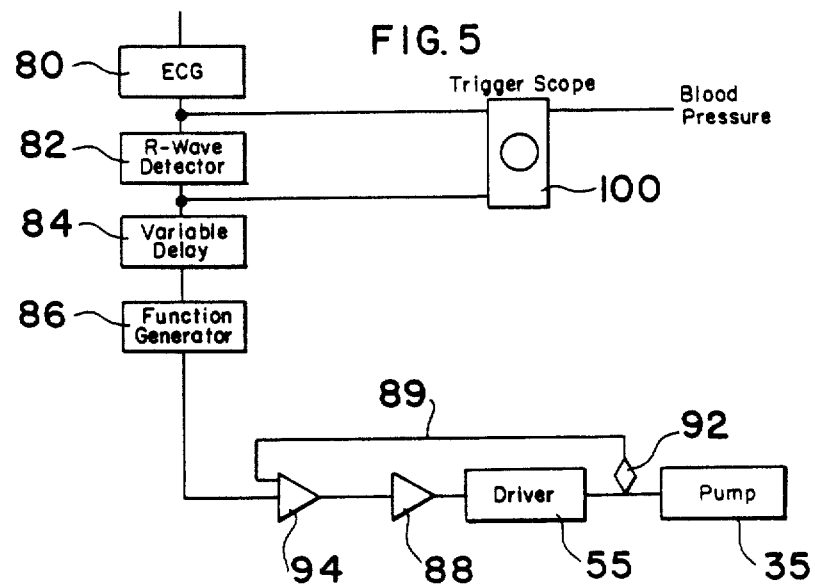
FIG. 5 is a schematic block diagram of an electronic control system for operating the augmenting pump shown in FIG. 1 and u.

The augmentation pump system of the invention includes two major parts which are the electro-mechanical assembly shown in FIG. 1 and its electronic control system shown in FIG. 5. The three catheter portions 12, 16 and 18 are combined to form one integral part, but the portions may have different durometers or stiffnesses. The two catheter portions 16 and 18 extend parallel to each other and are fused along a major portion of the catheter 10 and define the two passages 14 and 17, respectively. The distal end of the medication catheter 18 is open, and the end portion 19 extends through and past the inflatable catheter tip portion 12 so that the catheter tip portion 12 surrounds the medication catheter end portion 19. The outer or proximal end of the catheter tube 16 is attached to an augmentation pump 35, and the outer or proximal end of the catheter tube 18 is attached to a medication injector pump 36.

The augmentation pump 35 is designed to deliver and withdraw liquid fluid from the tip portion 12 and includes a pump body or housing 38 having a tubular tip portion 39 which is coupled to the outer end of the catheter tube 16. The housing 38 has a bottom flange 42 and receives a cylindrical rod or piston 44. A bellows-type rolling diaphragm 46 extends over the piston 44 and has an outwardly projecting peripheral flange portion which is clamped and sealed to the housing flange 42 by concentric sleeve 48. The catheter 10, pump housing 38 and attached diaphragm 46 form a sealed disposable unit which is prefilled with a predetermined volume of hydraulic fluid such as the saline solution mentioned above.

The pump housing flange 42 is secured to a tubular coupling housing 52 which has a base flange 53 secured to a pump driver or exciter 55 having a reciprocating or pulsating piston 56 coupled to the pump piston 44. The pump driver or exciter 55 is adjustable or controllable for selecting the amplitude and frequency of pulsation or reciprocation of the piston 56 and the pump piston 44. This control provides for precisely selecting the frequency of inflation and deflation of the catheter tip portion 12 by movement of the hydraulic fluid captured within the tip portion 12 and catheter passage 14 and within the pump housing 38 above the diaphragm 46. The driver 55 has sufficient power to overcome the viscous friction of the liquid within the catheter passage 14 and also to overcome the arterial or aortic pressure which opposes inflation of the catheter tip portion 12.

As mentioned above, permanent connections are used to make the catheter 10 and pump 35 assembly as an integral self contained unit. The augmenting tip 12, augmentation catheter passage 14, and the chamber of the augmentation pump housing 38 are prefilled with the pumping liquid and are supplied in sealed sterilized packages. The unit is quickly attached to the driver or exciter 55 immediately before its use and is disposed of after treatment.

Different types of drivers or exciters 55 may be used depending upon the special requirements of application of the system. One type of pump driver is an electromagnetic exciter 55 of sufficient power output, frequency range, and range of displacement amplitude for the piston 56. Another type of driver is an electrical stepping motor which provides for precise control of the piston 44 of the augmentation pump 35. The electromagnetic exciter 55 connects with the coupler housing 52 which confines linear bearing for guiding the piston 56 to assure accurate reciprocating movement of the piston 56. The outer end of the piston 56 is attached by a quick coupling device (not shown) to the augmentation pump piston 44. Either the exciter 55 or coupling housing 52 is preferably provided with a mechanical stop to limit inflation of the catheter tip 12 to a maximum safe level.

Figure 6:
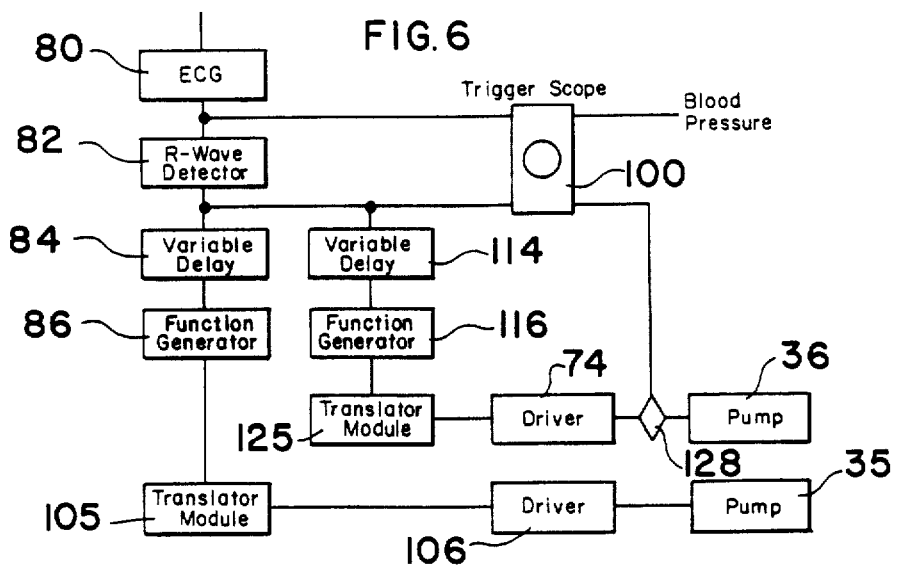
FIG. 6 is another schematic block diagram of an electronic control system for operating both the augmenting pump and medication pump shown in FIG. 1.

The operation of the pump 35 and catheter 10 produces a high speed alternating or pulsating action of the tip portion 12 at a frequency substantially above the normal pulse frequency of the heart. For example, as shown in FIG. 6, the tip portion 12 is pulsed at a frequency of about 20 Hz. so that nine or ten pulses are produced during the diastolic and part of the systolic or contraction period of each heart pulse. The dynamic characteristics of all parts involved, such as the tip portion 12, the catheter tube 16, the augmentation pump 35 and the driver 55 are selected to assure a high speed operation over a sufficient range of frequencies. This requirement determines the type of material and wall thickness used for the tube portion 16 and tip portion 12. The elastic and inertial properties of the pump 35 and driver 55 are adapted by selecting the moving parts with the correct mass and by adding elastic elements.

The injection pump 36 delivers medication through the medication catheter tube 18. The delivery is controlled as to the amount injected and as to the time of injection. For example, the injection may be made at one time or in any number of installments at any intervals of time and in any synchronization with respect to the cardiac cycle of the patient or in relation to the inflation and deflation of the tip portion 12. The medication injection system illustrated, includes a conventional syringe 62 which is coupled to the catheter tube 18 and has a plunger or piston 63 attached to an actuating plate 64. The plate 64 is supported for linear movement by a plurality of guide rods 67 which extend between a set of end plates 68 and 71. The actuating plate 64 also has a threaded hole which receives a lead screw 73 driven by a reversible electrical stepping motor 74 mounted on the end support plate 71.

Thus rotation of the lead screw 73 by actuation of the stepping motor 74 controls the displacement of the piston 63 of the syringe 62 and thereby controls the injection of the medication from the syringe 62 through the catheter tube 18 and its tip or end portion 19. Small incremental rotation of the lead screw 73 provides for accurate injection of a very small volume of medication in timed relation with the actuation of the augmentation pump 35. A three way valve (not shown) could be installed in the catheter tube 18 in order that the passage 17 may also be used for sensing and monitoring aortic blood pressure.

Referring to FIG. 5, an electronic control system controls the augmentation pump driver or electromagnetic exciter 55 for selecting the volume of liquid displaced into the inflatable tip portion 12 and the frequency of inflation. The system also activates the augmenting tip inflation in relation to events occurring during the cardiac cycle by receiving an input signal from an electrocardiogram (ECG) 80 which is monitoring the patient's heart pulse. The R-wave from an R-wave detector 82 is used as a signal which triggers the activation of the exciter 55 after a variable delay period selected by adjusting a variable delay unit 84. The operator sets the delay period, the frequency and amplitude of pump action, the duration of pump action, and the inflation rate-time relation (for instance sinusoidal, triangular, rectangular, ramp, single step, succession of steps, etc.).

The operation of the augmentation pump exciter 55 is controlled by a function generator 86. The function generator is set to produce an alternating output signal of a selected frequency, amplitude and wave shape, and the output signal forms an input to a power amplifier 88 which feeds an amplified signal to the exciter 55.

Since the electromagnetic exciter 55 is not a "stiff" driver, a feed back loop 89 is used when a particular piston position must be held momentarily. The feed back loop 89 consists of a position transducer 92 attached to the piston 56 of the driver 55. The transducer 92 generates a signal in proportion to the piston displacement, and this signal is fed into a summing amplifier 94.

The summing ammplifier 94 is inserted between the function generator 86 and the power amplifier 88 and determines the difference between the signal coming from the function generator 86 and the signal coming from the displacement transducer 92 and feeds this difference into the power amplifier 88. The output of the summing amplifier 94 and consequently the input to the power amplifier 88 is zero if the piston 56 is in the position as demanded by the function generator 86. Any discrepancy results in a signal from the summing amplifier 94 to the power amplifier 88 which, in turn, corrects the position of the piston 56.

Figure 4:
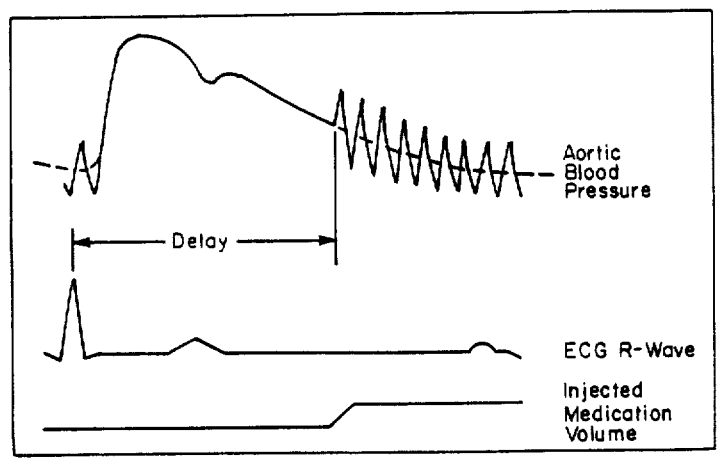
FIG. 4 is a typical display on a multi-channel oscilloscope connected to monitor the aortic pressure, the ECG R-wave, and the volume of injected medication.

The above description applies to the basic electronic instrumentation that is required to control the electromagnetic exciter 55 on a continuous basis if no triggering through an external signal is required. In some applications the driver or exciter 55 must be started and stopped in timed relation with the cardiac cycle. For example, the augmenting tip 12 must be evacuated and stopped at the end of the isometric contraction period, as shown in FIG. 4.

The R-wave from the electrocardiogram 80 is used as the point of reference for starting and stopping the exciter 55. Thus the patient's ECG is monitored and recorded on a multi-channel triggered oscilloscope 100 (FIG. 5) for observation. The ECG signal is also an input into a R-wave detector 82 which detects either the slope at the onset of the R-wave or the instance at which the R-wave exceeds a certain voltage level. The R-wave detector 82 then transmits a pulse to the variable delay unit 84.

If the pulse from the R-wave detector 82 was transmitted directly to the function generator 86, this would immediately trigger the function generator 86 and inflate the augmenting tip portion 12 during the systolic period. The tip portion 12 cannot be inflated during this period because of the related intolerable increase of ventricular pressure. The activation of the function generator 86 is therefore delayed in relation to the R- wave. The pulse from the R-wave detector 82 is transmitted to a circuit which delays the transmission to the function generator. The period of delay is adjustable and triggers the operation of the pump system in relation to the R-wave.

The ECG and aortic blood pressure are displayed on a multichannel triggered oscilloscope 100 so that the user may observe the effect of the augmenting pump operation on the aortic pressure pulses and their placement and duration within the cardiac cycle. This information enables the user to correct or adjust the placement of the series of pressure pulses within a cardiac cycle by adjusting the delay time. The display of the ECG and aortic pressure on the scope 100 is triggered by using the impulse from the R-wave detector 82. An almost standing picture of ECG and aortic pressure may be produced on the display screen of the oscilloscope 100, thereby greatly aiding the interpretation of both recordings.

The actuation of the tip portion 12 as to wave shape, frequency, amplitude, and period of operation in relation to cardiac events is selected according to each medical case. The aortic pressure, the ECG R-wave, the display of these signals on the trigger oscilloscope 100, the variable delay 84 and the function generator 86 may also be used for controlling a stepping motor and lead screwdriver 106 (FIG. 6) which may be used in place of the electromagnetic exciter 55. A stepping motor is an inherently stiff driver, and current is maintained on the motor windings when the motor is not being stepped for producing a high holding torque. The feed back loop consisting of the position transducer 92 and summing amplifier 94 is not essential for a stepping motor, but may be retained to serve as a precision control and safety control for the stepping motor. The power amplifier shown in FIG. 5 is replaced by a translator module 105 (FIG. 6) to control the operation of the stepping motor 106 which replaces the electromagnetic exciter 55.

As also shown in FIG. 6, the medication pump 36 is actuated by an electronic control which permits injection of medication in various ways such as in one-shot or in successive steps. This requires a control over the frequency of injection and the advance of the piston 63 in timed relation to either a cardiac event or to the inflation and deflation of the augmenting tip portion 12. The additional controls shown in FIG. 6 are the same controls as required for the control of the augmenting tip portion 12 and includes a variable delay 114, a function generator 116 and a translator module 125 for controlling the operation of the stepping motor 74 of the medication pump. The position of the injection pump 36 is sensed by a transducer 128 and displayed on the scope 100 so that the user may adjust the injection time in relation to aortic pressure or to other cadiac events by using the variable delay 114.

It is thus apparent from the above description that the method and apparatus of the invention may be used for treating pre-infarction angina, a pathophysiological state of regional tissue ischemia and decrease in normal muscle function. This state is usually caused by blockage of a coronary artery by an atherosclerotic intraluminal mass. The augmentation in accordance with the invention may be used to open up collateral vessels immediately after the coronary arteriography which identifies the cause. The catheter pulsating close to the coronary ostia to deliver short burst of energy is effective to open up the collateral vessels. In a coronary care unit, the pulsation may be monitored by existing equipment and its effectiveness measured by the return to normal function of the heart muscle and the improvement of the pre-infarcation angina.

The invention may also be used in connection with bypass open heart surgery when there exists a pathophysiological state of global heart hypoxia related to a low total body blood pressure and flow. The coronary blood flow may be completely stopped for periods of 5 to 10 minutes then reperfusion accomplished by unclamping of the thoracic aorta. This cycle may be repeated several times for a total bypass time of two hours, more or less. Return of normal cardiac muscle function may be delayed for one to three days, and regional ischemia/myocardial infarction occurs in 10 to 20% of the cases. The augmentation system may be used prior to bypass surgery and during each period of unclamping the aorta for reprefusion and for the one to three days following surgery. With the inflatable tip portion 12 close to the coronary arteries, the generation of pressure levels greater than the critical opening pressures of the numerous small coronary arteries would increase total blood flow to the cardiac tissues. The reversal of progressive hypoxia during bypass surgery and more rapid return toward normal function may be evaluated both at the surgical table and in the post-surgical intensive care unit. This technique should lessen the morbidity and mortality of open heart surgery.

The method and apparatus of the invention may also be used for a shocked a kidney which is a pathophysiological state in which a temporary decrease in systemic blood pressure is associated with a prolonged loss of normal kidney function. In spite of return to normal systemic blood pressure, regional blood flow to the kidney remains low. The decreased kidney function may not be detected for hours after the insult. Management presently consists of control of blood volume, electrolyte balance and stimulation of kidney function by tubular diuretics and osmolar solutions. During the prolonged ten to twenty days of kidney malfunction, renal dialysis may be necessary to sustain life. During and after an episode of hypotension, the augmenting tip portion 12 may be situated close to the renal artery take off from the abdominal aorta in order to reopen the small renal arteriols by the dynamic pressure wave form. The reestablishment of the renal vascular pressure gradient and tubular perfusion by the technique would prevent the shock kidney state and resultant morbidity.

Another use of the augmentation pump device of the invention is in connection with organ transplant when there normally occurs a pathophysiological state of whole organ anoxia resulting from abrupt loss of blood flow and pressure during removal of the organ (kidney, heart, liver, etc.) from the donor's body. Implantation of the organ into the recipient's body and restoration of the blood flow by surgical anastomosis of the arteries and veins do not result in immediate return of tissue viability in the transplanted organ. The augmentation pump of the invention may be used in the donor's body prior to removal of the organ to maintain blood pressure above the critical closing pressure and in the receptor's body following the vessel anastomosis to exceed the critical opening pressure of the transplanted organ. Viability of tissues should be enhanced by this procedure during the critical period of removal and also to improve the organ function in the recipient's body.

The use of the device of this invention may be extended to additional medical cases by using an open-ended catheter. One specific application is the higher frequency pulsatile perfusion of preserved kidneys or other organs, or combinations of organs for the time period between the removal of the organ from the donor and implantation into the recipient. An optimal adjustment of the frequency of pulsatility results in a maximum of pulsatile energy to reach the small peripheral vessels. Subsequently, a complete penetration of the organ with fresh perfusate occurs.

Figure 7:
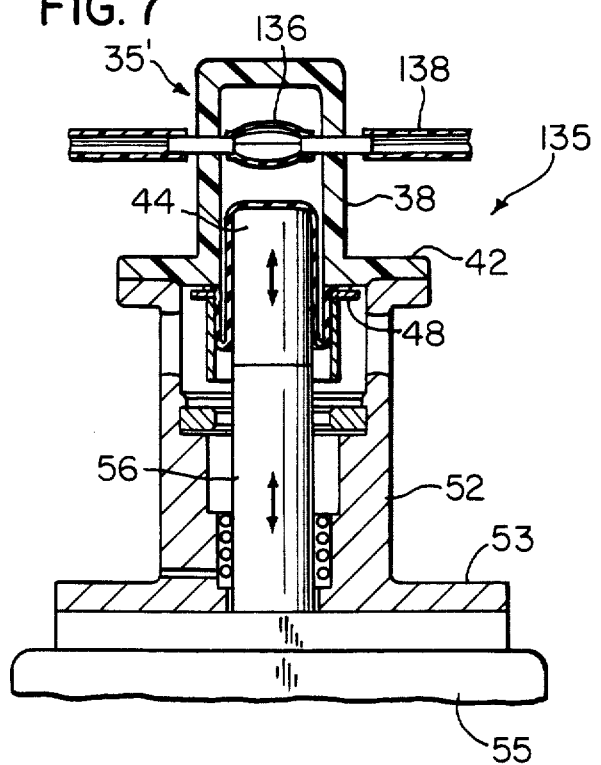
FIG. 7 illustrates an augmenting high frequency pulsatile pump device constructed in accordance with the invention and showing diagrammatically an open-ended catheter in axial section entering and leaving the pulsation chamber.
Figure 8:
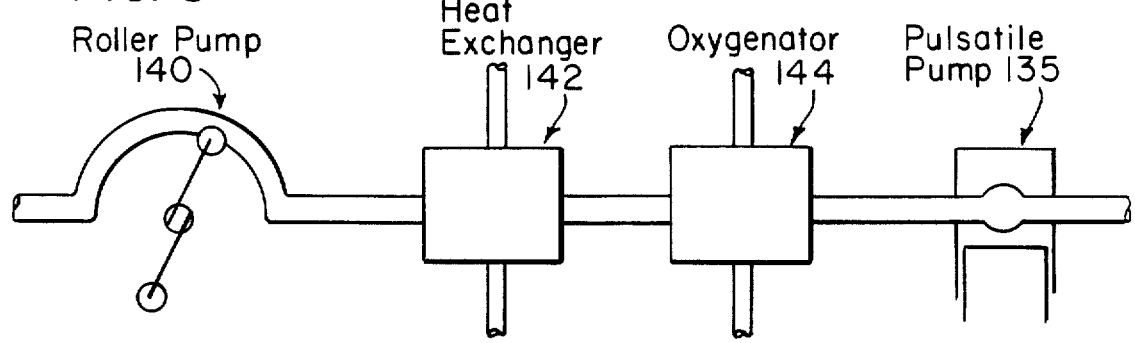
FIG. 8 is a schematic block diagram of a pulsatile perfusion system using an open ended perfusion catheter and the pulsatile pump device shown in FIG. 7.

FIG. 7 illustrates one possible pulsatile pump device 135 having a pump head 35' which is similar to the pump head 35 shown in FIG. 1 for use with the sealed catheter 10. The pump head 35' is attached to the tubular coupling housing 52 and receives a liquid which surrounds a tubular or bladder-like resilient pumping element 136 connected to a flexible conduit 138 through which blood or a blood substitute is circulated. The piston 44 within the pump head 35' is driven by the exciter 55. The previously described electronic equipment is used to control the piston motion as to frequency, stroke, and pulse shape. The electronic equipment can also be used to start and stop the piston in relation to other events. The pulsatile pumping device 135 may be incorporated in a standard perfusion circuit as shown schematically in FIG. 8. This circuit may be part of a closed-loop system and includes a roller pump 140, a heat exchanger 142, an oxygenator 144, and the pulsatile pump device 135.

The open ended catheter can be equipped with a second narrow lumen (not shown) similar to the closed or sealed catheter 10. The narrow lumen can be attached to the medication injection pump 36, and the injection of medication can be controlled by the electronic control system as previously described. A three-way valve or a T-connector (not shown) could be installed in the catheter tube in order that the medication passage may also be used for sensing and monitoring the perfusion pressure at the entrance of the perfused organ or tissue. A monoluminal catheter may be used instead of a biluminal catheter. For that purpose the catheter is equipped with a T-connector in order to establish a catheter connection with the medication injection pump 36, specifically with the syringe 62. This catheter may again be equipped with a three-valve or T-connector in order that the medication passage may be used for sensing and monitoring the perfusion pressure in the perfusion catheter.

While the methods and forms of pump apparatus herein described constitute preferred embodiments of the invention, it is to be understood that the invention is not limited to these precise methods and forms of apparatus described, and that changes may be made therein without departing from the scope and spirit of the invention as defined in the appended claims.

The invention having thus been described, the following is claimed:

1. A method for perfusing a body organ or tissue with blood or a blood substitute, comprising the steps of connecting the organ or tissue to pump means with a conduit, and pulsating the blood or blood substitute within the tissue or organ by operating the pump means at a frequency substantially greater than the normal pulsation frequency of the heart to produce an amplified dynamic pressure wave form in the blood or blood substitute within the microcirculatory vessels to increase the penetration of the blood or blood substitute into the body tissue or organ.

2. A method as defined in claim 1 and including the steps of monitoring the pulsation of the heart, and producing repetitive trains of pulses in timed relation with the pulsation of the heart.

3. A method as defined in claim 2 wherein the repetitive trains of pulses are produced during the diastolic period and/or isometric contraction period of the heart.

4. A method as defined in claim 1 and including the step of selecting the amplitude and frequency of pulsation in accordance with a specific physiological requirement.

5. A method as defined in claim 1 and including the step of directing the blood or blood substitute through a catheter forming the conduit and inserted into a vessel of the organ or tissue, and pulsating the blood or blood substitute within the catheter for transmitting pulsatile energy into the blood or blood substitute within the vessel.

6. A method as defined in claim 5 and including the step of pulsating the blood or blood substitute within the catheter in timed relation with heart pulses for generating and transmitting amplified pressure waves into tissue areas or organs during selected portions of the cardiac cycle.

7. A method as defined in claim 1 and including the step of producing pressure waves with sufficient amplitude to open previously collapsed small vessels within the tissue or organ.

8. A method as defined in claim 1 including the steps of monitoring the aortic blood pressure and the heart pulse of a patient, producing a visual display of the blood pressure and heart pulse, and pulsating the blood or blood substitute at the substantially greater frequency and in timed relation with the pulsation of the heart.

9. Apparatus for perfusing a body organ or tissue with blood or a blood substitute, comprising pump means, a conduit for connecting said pump means to the body tissue or organ, means driving said pump means for pulsating the blood or blood substitute within said body organ or tissue at a frequency substantially greater than the normal pulsation frequency of the heart, and means for varying the frequency and amplitude of said driving means according to the needs of the tissue or organ to produce an amplified dynamic pressure wave form in the blood or blood substitute within the microcirculatory vessels to increase the penetration of the blood or blood substitute into the body tissue or organ.

10. Apparatus as defined in claim 9 and including control means for operating said pump means in timed relation with the heart pulsation.

11. Apparatus as defined in claim 9 wherein said conduit comprises a catheter having a portion adapted to be inserted into a vessel for transmitting pulsatile energy to the blood or blood substitute within the vessel.

12. Apparatus as defined in claim 11 wherein said catheter includes an inflatable portion and confines a liquid.

13. Apparatus as defined in claim 9 wherein said conduit comprises a catheter adapted to be inserted into a vessel for directing a flow of the blood or blood substitute.

14. Apparatus as defined in claim 9 including means for sensing the pulsation of the heart, and time delay means for actuating said pump means in response to operation of said sensing means.

15. Apparatus as defined in claim 9 wherein said conduit comprises a catheter defining a primary passage for receiving a liquid which is pulsated and a secondary passage for receiving another liquid.

* * * * *